United States Patent [19]

Kukolja et al.

[11] 3,968,108

[45] July 6, 1976

[54] PROCESS FOR PREPARING A DESACETOXYCEPHALOSPORIN FROM A PENAM AND/OR A CEPHAM COMPOUND

[75] Inventors: Stjepan P. Kukolja, Indianapolis; Steven R. Lammert, Greenwood, both of Ind.

[73] Assignee: Eli Lilly and Company, Indianapolis, Ind.

[22] Filed: Mar. 27, 1974

[21] Appl. No.: 455,098

Related U.S. Application Data

[63] Continuation-in-part of Ser. No. 267,795, June 30, 1972, abandoned.

[52] U.S. Cl............................ 260/243 C; 260/239.1; 260/239.3 B
[51] Int. Cl.².............. C07D 501/10; C07D 501/04
[58] Field of Search....... 260/243 C, 239.1, 239.3 B

[56] References Cited
UNITED STATES PATENTS 3,852,282   12/1974   Dolfini ............................ 260/243 C

*Primary Examiner*—Alton D. Rollins
*Assistant Examiner*—David E. Wheeler
*Attorney, Agent, or Firm*—William C. Martens, Jr.; Everet F. Smith

[57] ABSTRACT

A 3α-methyl-3β-halocepham compound and/or a 2α-methyl-2β-halomethylpenam compound is converted to a mixture comprising a 3-methyl-3-cephem (desacetoxycephalosporin), a 3α-methyl-3β-acyloxycepham, and a 2α-methyl-2β-acyloxymethylpenam by reaction of said 3-halocepham compound and/or said 2-halomethylpenam compound with a silver salt of a lower alkyl carboxylic acid or a cycloalkyl carboxylic acid.

13 Claims, No Drawings

PROCESS FOR PREPARING A DESACETOXYCEPHALOSPORIN FROM A PENAM AND/OR A CEPHAM COMPOUND

CROSS REFERENCE

This application is a continuation-in-part of Application Ser. No. 267,795, filed June 30, 1972 now abandoned.

BACKGROUND OF THE INVENTION

The cephalosporin antibiotics have recently achieved considerable success as therapeutic agents for the treatment of infectious diseases of man. This class of antibiotics is produced by two known general methods. In the first of these methods, cephalosporin C is produced by culturing the organism *Cephalosporium acremonium*, Newton and Abraham, Biochem. J., 62, 651 (1956). Cleavage of the α-aminoadipoyl side chain of cephalosporin C according to the method described in U.S. Pat. No. 3,188,311 affords 7-aminocephalosporanic acid (7-ACA). Acylation of 7-ACA with an appropriate acyl halide, as, for example, thiophene-2-acetyl chloride, yields the expected 7-acylamidocephalosporanic acid antibiotic. The cephalosporin antibiotics obtained from cephalosporin C according to this method are derivatives of cephalosporanic acid which possesses an acetoxymethyl group attached at the 3-position of the cephalosporin nucleus. According to the cephem nomenclature system for the cephalosporins, the cephalosporin antibiotics obtained from cephalosporin C are named 7-acylamido-3-acetoxymethyl-3-cephem-4-carboxylic acids.

The method by which the cephalosporin antibiotics are produced involves the chemical conversion of a penicillin antibiotic. This method, described in U.S. Pat. No. 3,275,626, involves the conversion of the thiazolidine ring of a penicillin into the dihydrothiazine ring of a cephalosporin. The fused β-lactam ring of the penicillin molecule remains intact during the conversion. This chemical conversion is carried out by heating a penicillin sulfoxide in the presence of an acidic reagent, such as acetic anhydride, to obtain predominantly a 7-acylamido-3-methyl-3-cephem-4-carboxylic acid ester (a desacetoxycephalosporanic acid) and a 7-acylamido-3-methyl-3-acyloxycepham-4-carboxylic acid ester. Also produced in the chemical conversion process is a 2-acyloxymethylpenicillin, otherwise designated as a 6-acylamido-2-methyl-2-acyloxymethylpenam-3-carboxylic acid.

U.S. Pat. No. 3,275,626 additionally discusses the possibility of converting a penicillin sulfoxide by heating it in the presence of any of various acidic reagents. The ultimate antibiotic substances which form from such reactions will depend to some extent upon the particular acid which is employed, with the substituents present in the acid as well as the particular structure and relative strength of the acid having some effect upon the products formed.

In carrying out the reaction of a penicillin sulfoxide ester with thionyl chloride, it has been found that the following products can be produced:

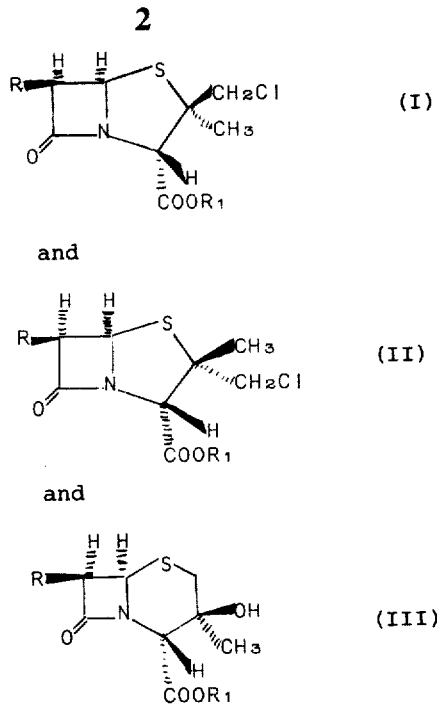

It further has been found that the 2α-methyl-2β-chloromethylpenam (I above) is unstable and gradually rearranges to the corresponding 3α-methyl-3β-chlorocepham of the formula

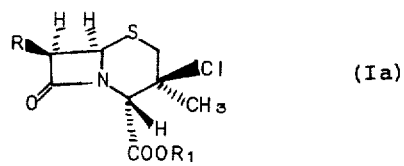

This rearrangement occurs at room temperature over a period of several days. The rearrangement can be greatly accelerated by subjecting the penam to an elevated temperature, for example, from about 50°C. to about 100°C., under which conditions the rearrangement can be accomplished in as little as one hour. Conversion to the corresponding 3α-methyl-3β-chlorocepham can also be effected by maintaining the unstable penam in a suitable inert solvent on a chromatographic column for a period of from about 24 to about 72 hours and then eluting the cepham product from the column.

In accordance with this invention, it has now been descovered that is is possible to convert a 6-imido-2α-methyl-2β-halomethylpenam-3-carboxylic acid ester having a structure such as (I) above and/or a 7-imido-3α-methyl-3β-halocepham-4-carboxylic acid ester obtainable by rearrangement from the aforementioned 2β-halomethylpenam and having a structure such as (Ia) above to an active 3-methyl-3-cephem antibiotic, a 3-methyl-3-acyloxycepham, and a 2-methyl-2-acyloxymethylpenam (penicillin) ring structure.

SUMMARY OF THE INVENTION

The present invention is directed to a process for preparing a mixture comprising a compound of the formula IV

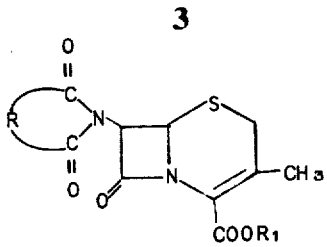

a compound of the formula V

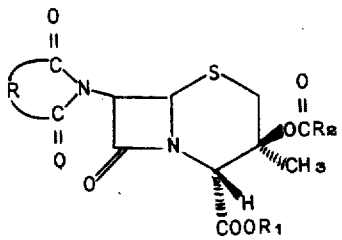

and a compound of the formula VI

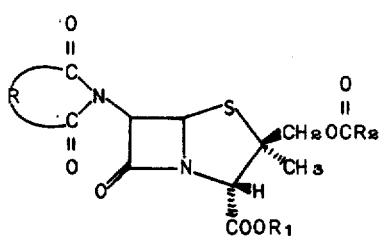

which comprises reacting a compound of the formula

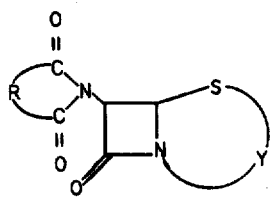

in which Y is

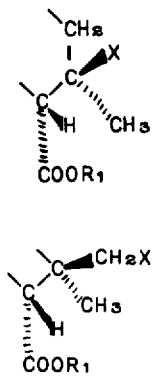

or a mixture of the two, with a compound of the formula

in which, in the above formulae, R is a residue of an imide derived from a dicarboxylic acid, $R_1$ is a carboxy protecting group, $R_2$ is $C_1$-$C_4$ alkyl or $C_5$-$C_6$ cycloalkyl, and X is chlorine or bromine.

DETAILED DESCRIPTION OF THE INVENTION

The process of this invention is carried out by contacting a 6-imido-2α-methyl-2β-halomethylpenam-3-carboxylic acid ester or a 7-imido-3α-methyl-3β-halocepham-4-carboxylic acid ester or a mixture of the two with a silver salt having the formula

in which $R_2$ is an alkyl group having from 1 to 4 carbon atoms or a cycloalkyl group having 5 or 6 carbon atoms.

The reaction preferably is carried out at a temperature within the range of from about 0°C. to about 100°C. More preferably, the temperature of reaction is between 20°C. and 85°C. Typically, the reaction is very rapid, and the time of reaction ranges from about 5 minutes to about 1 hour, with the reaction time to some degree being dependent upon the particular reactants which are employed as well as the temperature at which the reaction is carried out. Normally, the higher the temperature of reaction the shorter the necessary reaction time. Usually, the reaction is complete after the reactants have been maintained at the selected reaction temperature for about 5–10 minutes.

The conversion of the 2-halomethylpenam or the 3-halocepham compound preferably is carried out in the presence of a suitable solvent, specifically one which is inert to the reactants and which will facilitate adequate mixing of the reactants. Suitable solvents are those which are capable of dissolving both the silver salt and the halomethylpenam and/or the halocepham compound and which have a boiling point at least as high as the intended temperature of reaction. Such solvents include, for example, ketones, such as acetone, and the like, and lower alkyl carboxylic acids such as acetic acid, propionic acid, butyric acid, isobutyric acid, and the like. Preferably, if a carboxylic acid is employed as solvent, the anion of the acid solvent will be the same as that of the silver salt which is employed as reactant.

The conversion of the 2-halomethylpenam and/or the 3-halocepham compound is accomplished in the presence of a silver salt of a carboxylic acid. Suitable silver salts include silver acetate, silver propionate, silver n-butyrate, silver isobutyrate, silver n-valerate, silver trimethylacetate, silver α-methylbutyrate, silver β-methylbutyrate, silver cyclopentanecarboxylate, and silver cyclohexanecarboxylate. Preferably, the silver salt which is employed is silver acetate.

The reaction of the silver salt with the 2-halomethylpenam and/or the 3-halocepham is equimolar, and therefore at least one mole of the silver compound is required per each mole of the 2-halomethylpenam and/or 3-halocepham. Usually from about one to about two moles of the silver compound per mole of the 2-halomethylpenam and/or the 3-halocepham will be employed, and, preferably, an excess of the silver compound will be present, such as, for example, from about 1.1 to about 1.5 moles of the silver compound per each mole of the penam or cepham compound.

As mentioned hereinabove, the compounds used as starting material in the process of this invention can be prepared using techniques described in U.S. Pat. No. 3,275,626. These compounds also are available in accordance with the process described in United States Application Ser. No. 455,444 filed of even date herewith now Pat. No. 3,932,387, 1/13/76. This process involves the reaction of a 7-imido-3α-methyl-3β-hydroxycepham-4-carboxylic acid ester with a halogen reagent in the presence of an alkaline reagent to produce the 2-halomethylpenam starting material of the process of this invention. This penam starting material will rearrange over a period of time to the corresponding 3-halocepham starting material.

The 2-halomethylpenam starting material has the following formula:

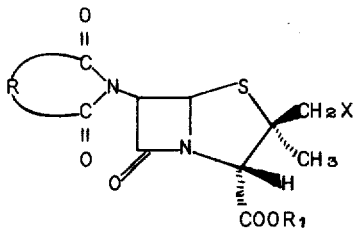

and the 3-halocepham starting material has the following formula

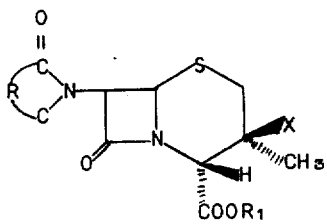

$R_1$ in the above formulae as well as in the products of the process of this invention denotes a carboxy protecting group. The nature of the carboxy protecting group is not important, and any of those known in the art can be used. Preferably, however, this group is the residue of an ester function which is removable by acid treatment or by hydrogenation. Preferred carboxy protecting groups include, for example, $C_1$-$C_4$ alkyl, 2,2,2-trihaloethyl, benzyl, p-nitrobenzyl, succinimidomethyl, phthalimidomethyl, p-methoxybenzyl, benzhydryl, $C_2$-$C_6$ alkanoyloxymethyl, or phenacyl, in any of the above of which halo denotes chlorine, bromine, or iodine.

Specific illustrations of the preferred ester residues of the carboxyl group of the 3-halocepham compound used in the process of this invention include, for example, methyl, ethyl, n-propyl, isopropyl, n-butyl, sec-butyl, isobutyl, t-butyl, 2,2,2-trichloroethyl, 2,2,2-tribromoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, and the like.

Highly preferred ester residues are methyl, benzyl, p-nitrobenzyl, p-methoxybenzyl, benzhydryl, and 2,2,2-trichloroethyl.

In the above formulae as well as in those depicting the products of the process of this invention, the cyclic imide radical defined by R taken together with the nitrogen-dicarbonyl combination to which it is bonded can be obtained by reacting the precursor of the penam or cepham starting material, such as the 6-amino group of 6-aminopenicillanic acid (6-APA) or an ester of 6-APA with a dicarboxylic acid or anhydride or other reactive variant thereof, and treating the resulting derivative with a $C_1$-$C_4$ alkyl haloformate, for example, ethyl chloroformate, in the presence of an organic base.

Preferably, R is $C_2$-$C_4$ alkylene, $C_2$-$C_4$ alkenylene, -$CH_2$-Y-$CH_2$- in which Y is oxygen or sulfur, 1,2-cylohexylene, 1,2-phenylene, 1,2-cyclohexenylene, or substituted derivatives of any of these having from 1 to 4 substituents selected from the group consisting of $C_1$-$C_3$ alkyl, $C_1$-$C_3$ alkoxy, and nitro. More preferably, R is $C_2$-$C_4$ alkylene, $C_2$-$C_4$ alkenylene, -$CH_2$-Y-$CH_2$- in which Y is oxygen or sulfur, 1,2-cyclohexylene, 1,2-phenylene, or 1,2-cyclohexenylene, each of which is unsubstituted or singly substituted with any of the aforementioned substituents. Typically, R represents the residue of a $C_4$ to $C_{10}$ dicarboxylic acid, and the cyclic imide thus represented is prepared from such dicarboxylic acid, its anhydride, or an appropriate reactive variant thereof. Cyclic imides can be prepared, for example, from acids such as succinic, maleic, glutaric, diglycolic, thiodiglycolic, phthalic, and the like, as well as from cyclohexane-1,2-dicarboxylic, 3-cyclohexene-1,2-dicarboxylic, alkyl substituted dicarboxylic acids or anhydrides such as 4,5-dimethylphthalic, tetramethylphthalic, 4-methylphthalic, nitro substituted dicarboxylic acids and anhydrides such as 3-nitrophthalic acid, alkyl substituted dicarboxylic acids and anhydrides such as methylmaleic acid, as well as related compounds and compounds of similar reactivities. Additional examples of cyclic anhydrides of the type defined are found in the prior art such as in the *Journal of Organic Chemistry*, Volume 26, pp. 3365–3367 (September, 1961). 6-Phthalimidopenicillanic acid can also be prepared from 6-APA and N-carboethoxyphthalimide according to the procedure of Y. G. Perron et al., *Journal of Medicinal Chemistry*, Volume 5, (1962), p. 1016.

The thus-produced 6-imide-substituted penicillanic acid or ester can then be oxidized in accordance with known techniques to produce the penicillin sulfoxide. This sulfoxide, having an appropriate carboxy protecting group, can then be reacted in accordance with the teaching provided in U.S. Pat. No. 3,275,626 to produce the 2-halomethylpenam or 3-halocepham starting material.

The halo of the 2-halomethylpenam or the 3-halocepham starting material can be chlorine or bromine. The identity of the halogen in the starting material is determined by the particular halogen reagent which is used in the hereinbefore described processes for obtaining the 2-halomethylpenam or the 3-halocepham. Preferably, the starting material will be an ester of 6-imido-2α-methyl-2β-chloromethylpenam-3-carboxylic acid or an ester of 7-imido-3α-methyl-3β-chlorocepham-4-carboxylic acid.

The reaction of the 2-halomethylpenam and/or the 3-halocepham compound in accordance with the process of this invention accomplishes the production of a desacetoxycephalosporin (3-methyl-3-cephem).

The desacetoxycephalosporins produced by this invention are convertible to active antibiotics by cleavage of the ester function in the 4-position. Deesterification can be achieved by treating the ester with an acid such as trifluoroacetic acid, hydrochloric acid, and the like, or with zinc and acid, such as formic acid, acetic acid, or hydrochloric acid. It can likewise be accomplished by hydrogenating the ester in the presence of palladium, rhodium, or a compound thereof, in suspension or on a carrier such as barium sulfate, carbon alumina, or the like.

Furthermore, other active antibiotics can be obtained from the previously or subsequently deesterified 3-methyl-3-cephem compound either by opening the 7-imido substituent to form a 7-amido derivative or by cleaving the 7-imido substituent and acylating the resulting 7-aminodesacetoxycephalosporin (7-ADCA). Any of these conversions are accomplished using recognized techniques.

Representative of the product conversions which are available in accordance with the process of this invention are the following. It will be understood, however, that the ratio of products may vary depending upon the particular reactants which are employed, the relative quantities of reactants, and the conditions of reaction.

Methyl 6-phthalimido-2α-chloromethylpenam-3-carboxylate and/or methyl 7-phthalimido-3α-methyl-3β-chlorocepham-4-carboxylate to methyl 7-phthalimido-3-methyl-3-cephem-4-carboxylate, methyl 7-phthalimido-3α-methyl-3β-acyloxycepham-4-carboxylate, and methyl 6-phthalimido-2α-methyl-2β-acyloxymethylpenam-3-carboxylate.

2,2,2-Trichloroethyl 6-phthalimido-2α-methyl-2β-chloromethylpenam-3-carboxylate and/or 2,2,2-trichloroethyl 7-phthalimido-3α-methyl-3β-chlorocepham-4-carboxylate to 2,2,2-trichloroethyl 7-phthalimido-3-methyl-3-cephem-4-carboxylate, 2,2,2-trichloroethyl 7-phthalimido-3α-methyl-3β-acyloxycepham-4-carboxylate, and 2,2,2-trichloroethyl 6-phthalimido-2α-methyl-2β-acyloxymethylpenam-3-carboxylate.

p-Nitrobenzyl 6-phthalimido-2α-methyl-2β-chloromethylpenam-3-carboxylate and/or p-nitrobenzyl 7-phthalimido-3α-methyl-3β-chlorocepham-4-carboxylate to p-nitrobenzyl 7-phthalimido-3-methyl-3-cephem-4-carboxylate, p-nitrobenzyl 7-phthalimido-3α-methyl-3β-acyloxycepham-4-carboxylate, and p-nitrobenzyl 6-phthalimido-2α-methyl-2β-acyloxymethylpenam-3-carboxylate.

Benzyl 6-succinimido-2α-methyl-2β-chloromethylpenam-3-carboxylate and/or benzyl 7-succinimido-3α-methyl-3β-chlorocepham-4-carboxylate to benzyl 7-succinimido-3-methyl-3-cephem-4-carboxylate, benzyl 7-succinimido-3α-methyl-3β-acyloxycepham-4-carboxylate, and benzyl 6-succinimido-2α-methyl-2β-acyloxymethylpenam-3-carboxylate.

Benzhydryl 6-phthalimido-2α-methyl-2β-chloromethylpenam-3-carboxylate and/or benzhydryl 7-phthalimido-3α-methyl-3β-chlorocepham-4-carboxylate to benzhydryl 7-phthalimido-3-methyl-3-cephem-4-carboxylate, benzhydryl 7-phthalimido-3α-methyl-3β-acyloxycepham-4-carboxylate, and benzhydryl 6-phthalimido-2α-methyl-2β-acyloxymethyl-penam-3-carboxylate.

t-Butyl 6-glutarimido-2α-methyl-2β-chloromethylpenam-3-carboxylate and/or t-butyl 7-glutarimido-3α-methyl-3β-chlorocepham-4-carboxylate to t-butyl 7-glutarimido-3-methyl-3-cephem-4-carboxylate, t-butyl 7-glutarimido-3α-methyl-3β-acyloxy-cepham-4-carboxylate, and t-butyl 6-glutarimido-2α-methyl-2β-acyloxymethylpenam-3-carboxylate.

p-Nitrobenzyl 6-diglycolimido-2α-methyl-2β-chloromethylpenam-3-carboxylate and/or p-nitrobenzyl 7-diglycolimido-3α-methyl-3β-Chlorocepham-4-carboxylate to p-nitrobenzyl 7-diglycolimido-3-methyl-3-cephem-4-carboxylate, p-nitrobenzyl 7-diglycolimido-3α-methyl-3β-acyloxycepham-4-carboxylate, and p-nitrobenzyl 6-diglycolimido-2α-methyl-2β-acyloxymethylpenam-3-carboxylate.

Benzhydryl 6-(3'-isopropylphthalimido)-2α-methyl-2β-chloromethylpenam-3-carboxylate and/or benzhydryl 7-(3'-isopropylphthalimido)-3α-methyl-3β-chloroceham-4-carboxylate to benzhydryl 7-(3'-isopropylphthalimido)-3-methyl-3-cephem-4-carboxylate, benzhydryl 7-(3'-isopropylphthalimido)-3α-methyl-3βacyloxycepham-4-carboxylate, and benzhydryl 6-(3'-isopropylphthalimido)-2α-methyl-2β-acyloxymethylpenam-3-carboxylate.

p-Nitrobenzyl 6-tetramethylphthalimido-2α-methyl-2β-chloromethylpenam-3-carboxylate and/or p-nitrobenzyl 7-tetramethylphthalimido-3α-methyl-3β-chlorocepham-4-carboxylate to p-nitrobenzyl 7-tetramethylphthalimido-3-methyl-3-cephem-4-carboxylate, p-nitrobenzyl 7-tetramethylphthalimido-3α-methyl-3β-acyloxycepham-4-carboxylate, and p-nitrobenzyl 6-tetramethylphthalimido-2α-methyl-2β-acyloxymethylpenam-3-carboxylate.

p-Methoxybenzyl 6-(3'-nitrophthalimido)-2α-methyl-2β-chloromethylpenam-3-carboxylate and/or p-methoxybenzyl 7-(3'-nitrophthalimido)-3α-methyl-3β-chlorocepham-4-carboxylate to p-methoxybenzyl 7-(3'-nitrophthalimido)-3-methyl-3-cephem-4-carboxylate, p-methoxybenzyl 7-(3'-nitrophthalimido)-3α-methyl-3β-acyloxycepham-4-carboxylate, and p-methoxybenzyl 6-(3'-nitrophthalimido)-2α-methyl-2β-acyloxymethylpenam-3-carboxylate.

Phthalimidomethyl 6-(4',5'-dimethoxyphthalimido)-2α-methyl-2β-chloromethylpenam-3-carboxylate and/or phthalimidomethyl 7-(4',5'-dimethoxyphthalimido)-3α-methyl-3β-chlorocepham-4-carboxylate to phthalimidomethyl 7-(4',5'-dimethoxyphthalimido)-3-methyl-3-cephem-4-carboxylate, phthalimidomethyl 7-(4',5'-dimethoxyphthalimido)-3α-methyl-3β-acyloxycepham-4-carboxylate, and phthalimidomethyl 6-(4',-5'-dimethoxyphthalimido)-2α-methyl- 2β-acyloxymethylpenam-3-carboxylate.

Succinimidomethyl 6-hexahydrophthalimido-2α-methyl-2β-chloromethylpenam-3-carboxylate and/or succinimidomethyl 7-hexahydrophthalimido-3α-methyl-3β-chlorocepham-4-carboxylate to succinimidomethyl 7-hexahydrophthalimido-3-methyl-3-cephem-4-carboxylate, succinimidomethyl 7-hexahydrophthalimido-3α-methyl-3β-acyloxycepham-4-carboxylate, and succinimidomethyl 6-hexahydrophthalimido-2α-methyl-2β-acyloxymethylpenam-3-carboxylate.

p-Nitrobenzyl 6-diglycolimido-2α-methyl-2β-chloromethylpenam-3-carboxylate and/or p-nitrobenzyl 7-diglycolimido-3α-methyl-3β-chlorocepham-4-carboxylate to p-nitrobenzyl 7-diglycolimido-3-methyl-3-cephem-4-carboxylate, p-nitrobenzyl 7-diglycolimido-3α-methyl-3β-acyloxycepham-4-carboxylate, and p-nitrobenzyl 6-diglycolimido-2α-methyl-2β-acyloxymethylpenam-3-carboxylate.

Pivaloyloxymethyl 6-(1',2',3',6'-tetrahydrophthalimido)-2α-methyl-2β-chloromethylpenam-3-carboxylate and/or pivaloyloxymethyl 7-(1',2',3',6'-tetrahydrophthalimido)-3α-methyl-3β-chlorocepham-4-carboxylate to pivaloyloxymethyl 7-(1',2',3',6'-tetrahydrophthalimido)-3-methyl-3-cephem-4-carboxylate, pivaloyloxymethyl 7-(1',2',3',6'-tetrahydrophthalimido)-3α-methyl-3β-acyloxycepham-4-carboxylate, and pivaloyloxymethyl 6-(1',2',3',6'-tetrahydrophthalimido)-2α-methyl-2β-acyloxymethylpenam-3-carboxylate.

Acetoxymethyl 6-(3'-methylphthalimido)-2α-methyl-2β-chloromethylpenam-3-carboxylate and/or acetoxymethyl 7-(3'-methylphthalimido)-3α-methyl-3β-chlorocepham-4-carboxylate to acetoxymethyl 7-(3'-methylphthalimido)-3-methyl-3-cephem-4-carboxylate, acetocymethyl 7-(3'-methylphthalimido)-3α-methyl-3β-acyloxycepham-4-carboxylate, and acetoxymethyl 6-(3'-methylphthalimido)-2α-methyl-2β-acyloxymethylpenam-3-carboxylate.

Phenacyl 6-(4'-methoxyphthalimido)-2α-methyl-2β-chloromethylpenam-3-carboxylate and/or phenacyl 7-(4'-methoxyphthalimido)-3α-methyl-3β-chlorocepham-4-carboxylate to phenacyl 7-(4'-methoxyphthalimido)-3 -methyl-3 -cephem-4-carboxylate, and phenacyl 7-(4'-methoxyphthalimido)-3α-methyl-3β-acyloxymethylpenam-4-carboxylate, and phenacyl 6-(4'-methoxyphthalimido- 2α-methyl-2β-acyloxymethylpenam-3-carboxylate.

p-Nitrobenzyl 6-thioglycolimido-2α-methyl-2β-chloromethylpenam-3-carboxylate and/or p-nitrobenzyl 7-thioglycolimido-3α-methyl-3β-chlorocepham-4-carboxylate to p-nitrobenzyl 7-thioglycolimido-3-methyl-3-cephem-4-carboxylate, p-nitrobenzyl 7-thioglycolimido-3α-methyl-3β-acyloxycepham-4-carboxylate, and p-nitrobenzyl 6-thioglycolimido-2α-methyl-2β-acyloxymethylpenam-3-carboxylate.

Phenacyl 6-glutarimido-2α-methyl-2β-chloromethylpenam-3-carboxylate and/or phenacyl 7-glutarimido-3α-methyl- 3β-chlorocepham-4-carboxylate to phenacyl 7-glutarimido-33-cephem-4-carboxylate, phenacyl 7-glutarimido-3α-methyl-3β-acyloxycepham-4-carboxylate, and phenacyl 6-glutarimido-2α-methyl-2β-acyloxymethylpenam-3-carboxylate.

2,2,2-Trichloroethyl 6-(3'-isopropylphthalimido)-2α-methyl-2β-chloromethylpenam-3-carboxylate and/or 2,2,2-trichloroethyl 7-(3'-isopropylphthalimido)-3α-methyl-3β-chlorocepham-4-carboxylate to 2,2,2-trichloroethyl 7-(3'-isopropylphthalimido)-3-methyl-3-cephem-4-carboxylate, 2,2,2-trichloroethyl 7-(3'-isopropylphthalimido)-3α-methyl-3β-acyloxycepham-4-carboxylate, and 2,2,2-trichloroethyl 6-(3'-isopropylphthalimido)-2α-methyl-2β-acyloxymethylpenam-3-carboxylate.

p-Methoxybenzyl 6-(3'-methoxyphthalimido)-2α-methyl-2β-chloromethylpenam-3-carboxylate and/or p-methoxybenzyl 7-(3'-methoxyphthalimido)-3α-methyl-3β-chlorocepham-4-carboxylate to p-methoxybenzyl 7-(3'-methoxyphthalimido)-3-methyl-3-cephem-4-carboxylate, p-methoxybenzyl 7-(3'-methoxyphthalimido)-3α-methyl-3β-acyloxycepham-4-carboxylate, and p-methoxybenzyl 6-(3'-methoxyphthalimido)-2α-methyl-2β-acyloxymethylpenam-3-carboxylate.

p-Nitrobenzyl 6-(1',4',5',6'-tetrahydrophthalimido-2α-methyl-2β-chloromethylpenam-3-carboxylate and/or p-nitrobenzyl 7-(1',4',5',6'-tetrahydrophthalimido)-3α-methyl-3β-chlorocepham-4-carboxylate to p-nitrobenzyl 7-(1', 4',5',6'-tetrahydrophthalimido)-3-methyl-3-cephem-4-carboxylate, p-nitrobenzyl 7-(1',4',5',6'-tetrahydrophthalimido)-3α-methyl-3β-acyloxycepham- 4-carboxylate, and p-nitrobenzyl 6-(1',4',5',6'-tetrahydrophthalimido)-2α-methyl-2β-acyloxyymethylpenam-3-carboxylate.

It will be understood that, in the above representative conversions, a corresponding 2β-bromomethylpenam and/or 3β-bromocepham reactant can be substituted for any of the 2β-chloromethylpenam and/or 3β-chlorocepham reactants. Furthermore, the designation "acyloxy" appearing therein refers to the anion of the silver salt which is employed in the process of this invention. The acyloxy function thus conforms to any of the silver salt anions mentioned hereinabove as available for use in the process of this invention.

The products produced in accordance with the process of this invention can be isolated by conventional methods. These can include, for example, chromatographic separation, filtration, recrystallization, and the like.

This invention is further illustrated by reference to the examples which follow. It is not intended that this invention be limited in scope by reason of any of the examples provided herein.

Preparation of Methyl 6-Phthalimido-2α-methyl-2β-chloromethylpenam-3-carboxylate.

A solution of 2.25 g. (6 mmol) of methyl 6-phthalimido-2,2-dimethylpenam-3-carboxylate-1-oxide, 0.47 ml. (6.5 mmol) thionyl chloride, and 0.84 ml. (6 mmol) of triethylamine in 90 ml. of dry carbon tetrachloride was refluxed for 1 hr. The reaction mixture was then cooled and evaporated in vacuo to give a light yellow foam. Chromatography on 70 g. of acid washed silica gel yielded three fractions, the first of which contained 780 mg. (33%) of methyl 6-phthalimido-2α-methyl-2β-chlorometylpenam-3-carboxylate. Recrystallization from diethyl ether gave colorless needles: mp 107°–112°;$[\alpha]^{27}$ D 255.4° ($CH_3CN$); ir ($CHCl_3$) 1802 (β-lactam C=O), 1732 and 1785 (phthalimido C=O) and 1748 $cm^{-1}$ (ester C=O); nmr ($CDCl_3$) 95 (s, 3, 3,-$CH_3$), 230 (s, 3, Me ester), 246 (ABq, 2, J=24 Hz and J=12 Hz), 307 (s, 1, H-4), 344 (s, 2, β-lactam H's) and 472 Hz (m, 4, ArH).

Anal. Calcd for $C_{17}H_{15}ClN_2O_5S$: C, 51.71; H, 3.83; N, 7.10; O, 20.26; S, 8.12; Cl, 8.98. Found: C, 52.00; H, 4.01; N, 7.24; O, 20.25; S, 7.76; Cl, 9.04.

The second fraction (210 mg.) contained a 3:1 mixture (by nmr) of the 2β-chloromethylpenam methyl ester and the isomeric methyl 6-phthalimido-2α-chloromethylpenam-2β-methyl-3-carboxylate. The latter was obtained from a third fraction as a white foam (250 mg., 11%) which was recrystallized from $Et_2O$ to give colorless needles: mp 166°–167°;$[\alpha]^{27}$ D 221.0° ($CH_3CN$); ir ($CHCl_3$) 1803 (β-lactam C=O), 1745 and 1786 (phthalimido C=O), and 1737 $cm^{-1}$ (ester C=O); nmr ($CDCl_3$) 116 (s, 3, β-methyl), 229 (s, 3, methyl ester), 231 (ABq, 2, J=15 and J=11.5 Hz, $CH_2Cl$), 286 (s, 1, H-3), 340 (q, 2, J=4 Hz, β-lactam H's) and 470 Hz (m, 4, ArH).

Anal. Calcd for $C_{17}H_{15}$ $ClN_2O_5S$: C, 51.71, H, 3.83; N, 7.10. Found: C, 51.91; H, 3.72; N, 7.18.

Example 1

To a solution of 2.35 g. (6 mmol) of methyl 6-phthalimido-2α-methyl-2β-chloromethylpenam-3-carboxylate in 75 ml. of glacial acetic acid was added 1.10 g. (6.6 mmol) of silver acetate. The reaction mixture was heated on a steam bath for 15 minutes and then filtered to remove the silver chloride precipitate which formed. The filtrate was evaporated in vacuo to near dryness, and the residue was taken up in 80 ml. of ethyl acetate and washed with saturated $NaHCO_3$ solution (50 ml. × 2), water (50 ml.) and brine (50 ml.). After drying over $MgSO_4$ the ethyl acetate solution was evaporated in vacuo to a white foam. A thin-layer chromatography (tlc) (4:1-benzene:ethyl acetate) indicated a mixture of 3 products. Integration of the nmr showed a 3:3:1 mixture of methyl 7-phthalimido-3α-methyl-3β-acetoxycepham-4-carboxylate, methyl 6-phthalimido-2α-methyl-2β-acetoxymethylpenam-3-carboxylate, and methyl 7-phthalimido-3-methyl- 3-cephem-4-carboxylate, respectively. Chromatography on silica gel (5:95, ethyl acetate-benzene) gave 880 mg. of the 2β-acetoxymethylpenam (contaminated with a small amount of the 3-methyl-3-cephem): nmr (CDCl$_3$) 89 (s, 3, α-CH$_3$), 130 (s, 3, OAc), 230 (s, 3, Me ester), 270 ABq, 2, J=11 Hz and 12 Hz), 301 (s, 1, H-3), 343 (s, 2, β-lactam H's) and 470Hz (m, 4, ArH).

A second fraction contained 1.02 g. of a 4:3 (by nmr) mixture of methyl 6-phthalimido-2α-methyl-2β-acetoxymethylpenam-3-carboxylate and methyl 7-phthalimido-3α-methyl-3β-acetoxycepham-4-carboxylate, respectively. The structure of the latter was confirmed by comparison of the nmr with that of an authentic sample prepared in the following manner.

Fluorosulfonic acid (0.9 ml., 15 mmol) was added to a solution of methyl 7-phthalimido-3α-methyl-3β-hydroxycepham-4-carboxylate (1.51 g., 4 mmol) in 70 ml acetic acid at room temperature. The mixture was heated on a steam bath for 5 minutes, cooled, and evaporated in vacuo to near dryness. The resulting colorless syrup was taken up in 50 ml. of ethyl acetate and slurried with 30 ml. saturated sodium bicarbonate solution. The organic layer was separated and washed successively with saturated NaHCO$_3$ solution (20 ml.), water (30 ml.), and brine (40 ml.). After drying, the ethyl acetate solution was evaporated in vacuo to give a colorless foam. Recrystallization from ethyl acetate/cyclohexane gave 1.10 g. (63%) of white crystalline methyl 7-phthalimido-3-methyl-3-acetoxycepham-4-carboxylate (mp 146°-148°): nmr (CDCl3) 96 (3, s, 3-CH 3), 141 (3, s, ester CH$_3$), 298 (1, s, 4-H), 329 (2, q, J=4 Hz, β-lactam protons) and 478 Hz (4, m, ArH).

Anal. Calcd for C$_{19}$H$_{16}$N$_2$O$_7$S: C, 54.54; H, 4.34; N, 6.70; O, 26.77; S, 7.66. Found: C, 54.35; H, 4.58; N, 6.46; O, 26.51; S, 7.38.

EXAMPLE II

Methyl 6-phthalimido-2α-methyl-2β-chloromethylpenam-3-carboxylate (1.44 g.; 3.65 mmole) was chromatographed on a 4 × 70 cm. column packed with 80 g. (15 cm.) of acid washed silica gel. The 2β-chloromethylpenam compound was washed onto the column with 100 ml. (out of a total of 200 ml.) of toluene at an initial rate of 1.8 ml. per minute. The flow rate was then shut off, and the column was allowed to stand for 2.5 days. The column was then developed at 1.0 ml. per minute using a mixture containing 10 percent ethyl acetate in toluene. Fractions of 20 ml. each were collected. Fractions 41-80 gave 0.57 g. of methyl 7-phthalimido-3α-methyl-3β-chlorocepham-4-carboxylate: nmr (CDCl$_3$) 105 (s, 3, C$_3$-αCH$_3$); 184, 206 (ABq, 2, C$_2$-H); 297 (s, 1, C$_4$-H); 324 (d, 1, C$_6$-H); and 337 Hz (d, 1, C$_7$-H).

EXAMPLE III

To 100 mg. (0.25 mmole) of methyl 7-phthalimido-3α-methyl-3β-chlorocepham-4-carboxylate dissolved in 25 ml. of glacial acetic acid are added 100 mg. (0.59 mmole) of silver acetate. The resulting mixture is stirred and heated to reflux for 32 hours. The reaction mixture is then evaporated in vacuo to dryness. The residue is slurried with 10 ml. of chloroform and filtered. The reaction flask and precipitate are washed with 10 ml. of chloroform, and the chloroform is added to the filtrate. The filtrate is evaporated in vacuo to dryness. An nmr spectra shows the presence of methyl 7-phthalimido-3α-methyl-3β-acetoxycephan-4-carboxylate; methyl 7-phthalimido-3-methyl-3-cephem-4-carboxylate; and methyl 6-phthalimido-2α-methyl-2β-acetoxymethylpenam-3-carboxylate.

We claim:
1. A process for preparing a compound of the formula:

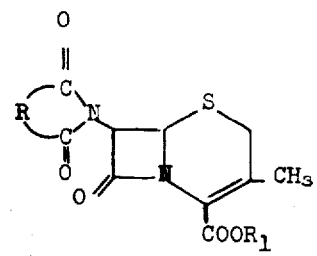

which comprises the step of reacting a compound of the formula:

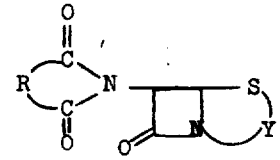

in which Y is

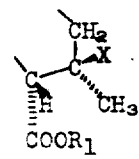

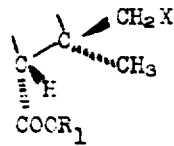

or a mixture of the two, with a compound of the formula

in which, in the above formulae, R is C$_2$-C$_4$ alkylene, C$_2$-C$_4$ alkenylene, -CH$_2$-Z-CH$_2$- in which Z is oxygen or sulfur, 1,2-cyclohexylene, 1,2-phenylene, 1,2-cyclohexenylene, or a monosubstituted derivative of any of the above having a substituent selected from the group consisting of C$_1$-C$_3$ alkyl, C$_1$-C$_3$ alkoxy, and nitro; R$_1$ is a carboxy protecting group; R$_2$ is C$_1$-C$_4$ alkyl or C$_5$-C$_6$ cycloalkyl; and X is chlorine or bromine.

2. Process of claim 1, in which R is C$_2$-C$_4$ alkylene, C$_2$-C$_4$ alkenylene, CH$_2$-Z-CH$_2$ in which Z is oxygen or sulfur, 1,2-cyclohexylene, 1,2-phenylene, or 1,2-cyclohexenylene.

3. Process of claim 2, in which $R_1$ is the residue of an ester group which is removable by hydrogenation or acid treatment.

4. Process of claim 3, in which $R_1$ is $C_1$-$C_4$ alkyl, 2,2,2-trihaloethyl, benzyl, p-nitrobenzyl, succinimidomethyl, phthalimidomethyl, p-methoxybenzyl, benzhydryl, $C_2$-$C_6$- alkanoyloxymethyl, or phenacyl.

5. Process of claim 4, in which Y is

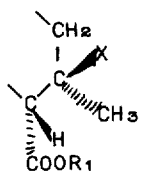

6. Process of claim 4, in which Y is

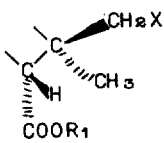

7. Process of claim 4, in which the starting material comprises a mixture in which Y is

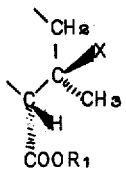 and 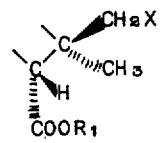

8. Process of claim 4, in which X is chloro.

9. Process of claim 8, in which $R_2$ is methyl.

10. Process of claim 9, in which R is 1,2-phenylene.

11. Process of claim 9, in which $R_1$ is methyl benzyl, p-nitrobenzyl, p-methoxybenzyl, benzhydryl, or 2,2,2-trichloroethyl.

12. Process of claim 11, in which $R_1$ is p-nitrobenzyl.

13. Process of claim 11, in which $R_1$ is p-methoxybenzyl.

* * * * *